United States Patent [19]
Czarnek et al.

[11] Patent Number: 5,613,936
[45] Date of Patent: Mar. 25, 1997

[54] STEREO LAPAROSCOPE APPARATUS

[75] Inventors: Robert Czarnek; Michael A. Saverino; Jack Kolff, all of Johnstown, Pa.

[73] Assignee: Concurrent Technologies Corp., Johnstown, Pa.

[21] Appl. No.: 392,094

[22] Filed: Feb. 22, 1995

[51] Int. Cl.$^6$ .............................. A61B 1/00; A61B 1/313
[52] U.S. Cl. ......................... 600/166; 600/129; 600/170; 600/173
[58] Field of Search ................................. 600/166, 111, 600/167, 170, 129, 130, 173; 359/464, 471, 475; 348/45; 356/241; 385/119

[56] References Cited

U.S. PATENT DOCUMENTS

| | | | |
|---|---|---|---|
| 3,520,587 | 7/1970 | Tasaki et al. | 600/166 |
| 3,561,432 | 2/1971 | Yamaki | 600/170 |
| 3,941,121 | 3/1976 | Olinger et al. | 600/167 |
| 4,873,572 | 10/1989 | Miyazaki et al. | 600/111 |
| 4,877,307 | 10/1989 | Kalmanash | 348/57 |
| 5,003,385 | 3/1991 | Sudo | 359/464 |
| 5,059,009 | 10/1991 | McKinley . | |
| 5,097,359 | 3/1992 | McKinley . | |
| 5,122,650 | 6/1992 | McKinley . | |
| 5,188,094 | 2/1993 | Adair | 600/131 |
| 5,222,477 | 6/1993 | Lia | 600/166 |

FOREIGN PATENT DOCUMENTS

| | | | |
|---|---|---|---|
| 4241938 | 6/1994 | Germany | 348/45 |
| 232524 | 11/1985 | Japan | 385/117 |
| 4016812 | 1/1992 | Japan | 600/166 |

OTHER PUBLICATIONS

*The World's Only Flexible Video Laparascope*, Distalvu™ 360 Video Laparascope, Welch Allyn Surgical Imagin Systems, Feb. 1995.
*StereoVU™ 3D Video Laparascope*, Welich Allyn Surgical Imaging Systems.
*UniversalVU™*, Welch Allyn Surgical Imaging Systems.
*3–D System With Two CCDs*, Welch Allyn Surgical Imaging Systems.

Primary Examiner—Richard J. Apley
Assistant Examiner—John P. Leubecker
Attorney, Agent, or Firm—Thorpe, North & Western

[57] ABSTRACT

A stereo laparoscope for producing a stereoscopic optical image of an intracorporeal region comprises an elongate tubular casing having side walls in which an illuminating window and left and right observation windows are disposed. A single, elongate, image transmitting optical fiber bundle is disposed within the casing, as are light emitting fibers for illuminating the intracorporeal region through the illuminating window. Left and right images are collected from the observation windows and alternately passed along the casing to the fiber bundle by a relay means comprising objective lenses, mirrors, a polarizing beam splitter and an optical switch. The left and right images are carried one at a time by the fiber bundle to a video display means which displays them to a viewer. Optical valves provide that the left image is viewed by the viewer's left and the right image is view by the viewer's right eye, to thereby produce a stereoscopic optical image. The left and right images are displayed at a rate of alternation that is faster than the flicker-sensing limit of the human eye, resulting in flicker free viewing.

29 Claims, 2 Drawing Sheets

STEREO LAPAROSCOPE APPARATUS

BACKGROUND OF THE INVENTION

1. The Field of the Invention

The present invention relates to apparatus and methods for producing a stereoscopic optical image. More particularly, the invention is directed to a stereo video laparoscope utilizing, in combination, a relay lens system, an optical switch and a single optical fiber bundle to provide a stereoscopic view of internal regions of the human body during diagnostic, surgical and other medical procedures.

2. The Background Art

Modern surgeons seek to perform necessary surgical procedures on a patient while minimizing the disturbance and destruction to intervening tissues and organs. To this end, medical endoscopes have been developed as an aid to diagnostic, surgical and other medical procedures. Medical endoscopes enable visual examination of body channels, cavities, spaces and internal organs through a natural opening or small incision, and thus without conventional surgery. Medical endoscopes are also useful for visual observation during surgery. Specific endoscopes have been developed for access to various body lumens and cavities. For example, laparoscopes, bronchoscopes, sigmoidoscopes, gastroscopes, and so forth, are all available. The main difference between these devices is the size of the instrument. However, the general configuration and method of use of such scopes are quite similar. Many of the body cavities and hollow conduits (e.g. peritoneal, abdominal, bronchial, lung, esophagal, etc.) can thus be accessed through endoscopic means, without surgical incisions and the resulting trauma to the patient.

Endoscopes typically include a long, thin tubular casing optically connected to a viewing mechanism. The tubular casing is narrow enough to insert through a small natural or surgical opening in the body. When the endoscope is inserted and positioned for use, an image of the object being viewed is formed at an inserted end thereof by an objective lens. The image is passed through a series of relay lenses down the cylinder to an eye lens or video camera at a viewing end of the endoscope. A major drawback to using an endoscope as a surgical aid is that it gives a monocular view and therefore no depth perception. Surgical procedures such as suction, irrigation, biopsy, incisions, suturing and cutting must be learned without the benefit of three dimensional visualization.

Endoscopes have recently been developed which produce the illusion of three dimensions or depth by combining two dimensional images. However, the mechanics of providing such a stereoscopic or three dimensional view require an increase in the size, weight and/or number of endoscopes, thus adding to the problem of limited portal entry space and convenience.

The stereoscopic effect is created by producing two optical images of the desired region, each image having a different point of view, such as a left image and a right image. It is known to incorporate two separate optical fiber bundles in parallel inside a single casing to add the advantages of fiberoptics to stereoscopic viewing. The two images are carried by the two optical fiber bundles, respectively, to left and right image sensors, which may comprise charge-coupled device (CCD) cameras or other image sensing devices. The sensing devices convert the left and right optical images into left and right video images, respectively. The video images are then presented as alternating left-right images on a viewing monitor to the user to thereby create a stereoscopic or three-dimensional optical view.

Although prior art endoscopes have succeeded in producing a stereoscopic or three dimensional effect, they are characterized by a number of disadvantages. The known stereoscopic instruments are not designed to give good stereoscopic viewing inside the larger body cavities such as the pleural and peritoneal cavities. Moreover, they require the use of two separate fiber bundles within a single casing. This requires two separate camera systems and sensing apparatus, with the attendant internal optics and electronics. This not only increases the cost, but also the size and weight of the device, making it less convenient to use.

Further, the use of two fiber bundles increases the diameter of the tubular casing, or requires a reduction in the size of the bundles, resulting in a loss of image resolution. The surgeon is thus forced to choose between a compact, lightweight endoscope which fails to offer three dimensional viewing, and an endoscope which offers three dimensional viewing but which is also relatively heavy, bulky, expensive and ill suited for inspection of the larger body cavities.

It is clear that there is a need for an economical endoscope which offers the advantages of fiberoptics and produces a stereoscopic optical image. There is a further need for such an endoscope which is compact and relatively lightweight, and which is suitable for inspecting the larger body cavities, without compromising the quality of the optical image. Although the industry continues to research alternate methods and devices for producing a stereoscopic optical image of an intracorporeal region, none of the methods or devices known to applicant has provided an acceptable device having the compact advantages of smaller size and weight, as well as cost competitiveness.

OBJECTS AND SUMMARY OF THE INVENTION

It is therefore an object of the present invention to provide an improved stereo endoscope for producing a stereoscopic optical image of an intracorporeal region of the human body.

It is an additional object of the invention to provide such a stereo endoscope which offers the advantages of fiberoptics and is relatively compact, light weight and easy to maneuver.

It is also an object of the invention to provide such a stereo endoscope which offers a high quality optical image but which is also economical.

It is still another object of the invention to provide such a stereo endoscope which is well suited for inspecting the larger body cavities.

The present invention is described in terms of a laparoscope to be used in inspecting intracorporeal regions of the human body, such as the peritoneal or abdominal cavities, during diagnostic, surgical or other medical procedures. However, it is to be understood that the principles of the present invention may be used in any medical endoscope, such as the thoracoscope, or in any other field of stereoscopic optical imaging. For example, in the industrial field, an industrial endoscope is used to inspect structures, components, damaged areas and the like in spaces which are relatively inaccessible, such as a damaged portion of the inner wall of a pipe or the interior of a jet engine. Those having ordinary skill in the field of this invention will appreciate the advantages of the invention, and its broad application to the general field of stereoscopic image production within spaces of limited size.

The above objects and others not specifically recited are realized in a specific illustrative embodiment of a stereo laparoscope apparatus for producing the illusion of a stereoscopic or three dimensional view of the abdominal cavity through a small incision. The stereo laparoscope includes a conventional elongate tubular casing having an illuminating window and left and right observation windows disposed in a distal extremity thereof, said distal extremity for insertion within the human body. A single, elongate optical fiber bundle is disposed within the casing. The end of the bundle positioned closest to the distal end of the casing is a receiving end including fiber tips for receiving optical images. Light emitting fibers are also disposed within the casing, and may be positioned spatially separate from the fiber bundle or upon the fiber bundle itself. The light emitting fibers emit light which is then projected upon a region external to the laparoscope to thereby cause said region to reflect light. The left and right observation windows receive the light reflected from the region to thereby provide left and right points of view, respectively, of said region.

Lenses are disposed within the casing for processing the light received from the left and right observation windows into left and right optical images. These images are conveyed through the casing by a relay means comprising mirrors, imaging lenses, a polarizing beam splitter, an optical switch and a focusing lens. The left and right images are processed by the beam splitter to have opposing polarities and are received simultaneously by the optical switch which alternately transmits them to the receiving end of the fiber bundle at a predetermined rate. The alternating optical images are thereby received one at a time by the fiber tips at the receiving end and carried one at a time through the fibers to the other or transmitting end of the bundle.

A camera apparatus receives the alternating left and right optical images from the transmitting end of the fiber bundle and presents them in tandem with the optical switch as alternating left-right images on a display means, such as a monitor, to the observer at said predetermined rate. This is accomplished with conventional video circuitry. The observer views the monitor through specialized glasses having optical valves or switches which channel the left-hand image to the left eye and the right-hand image to the right eye in tandem with the optical switch and monitor at said predetermined rate. Thus, the left eye sees only images from the left observation window of the endoscope and the right eye sees only images from the right observation window. The predetermined rate of alternation is faster than the flickersensing limit of the human eye, resulting in flicker free viewing.

In use, a physician makes a small incision in the abdominal cavity and inserts the distal end of the laparoscope therein so that said distal end resides within the abdominal cavity at a desired location. The physician can then inspect the location by viewing the three dimensional video image thereof displayed by the specialized glasses, maneuvering the laparoscope as desired in order to achieve an optimal view. The combination of the relay means with a single fiber bundle produces a stereoscopic or three dimensional image having resolution and image quality just as keen as that produced by a laparoscope utilizing two optical fiber bundles of the same quality. The resulting compactness and relative light weight of the laparoscope due to the elimination of an entire optical fiber bundle, one of the cameras and corresponding cables, makes it easier for the physician to maneuver the laparoscope which, under the press of surgery and other medical procedures, helps make the procedure more effective.

BRIEF DESCRIPTION OF THE DRAWINGS

The above and other objects, features and advantages of the invention will become apparent from a consideration of the subsequent detailed description presented in connection with the accompanying drawings in which.

DETAILED DESCRIPTION OF THE PRESENTLY PREFERRED EMBODIMENTS OF THE PRESENT INVENTION

Figure 1:
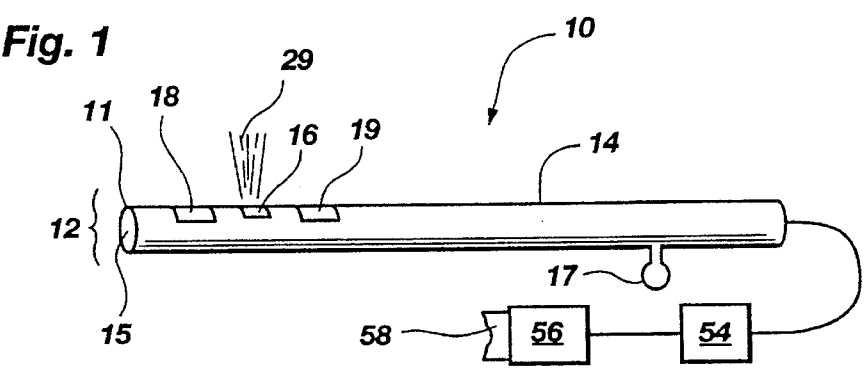
FIG. 1 is a perspective view of a stereo laparoscope made in accordance with the principles of the present invention.

Reference will now be made to the drawings wherein like structures will be provided with like reference numerals. A preferred embodiment of a stereo laparoscope having fixed focus imaging and fixed depth perception is illustrated in FIG. 1. Referring to FIG. 1, there is shown a stereo laparoscope, generally designated at 10, for inserting into the abdominal cavity through a small incision. The stereo laparoscope 10 comprises a hollow, elongate casing designated by bracket 12 having cylindrical side walls 14. An illuminating window 16 and left and right observation windows 18 and 19, respectively, are disposed in the side walls 14, preferably near distal extremity 11. A side mounted handle grip 17 for gripping by the user provides a natural feel.

Figure 2:
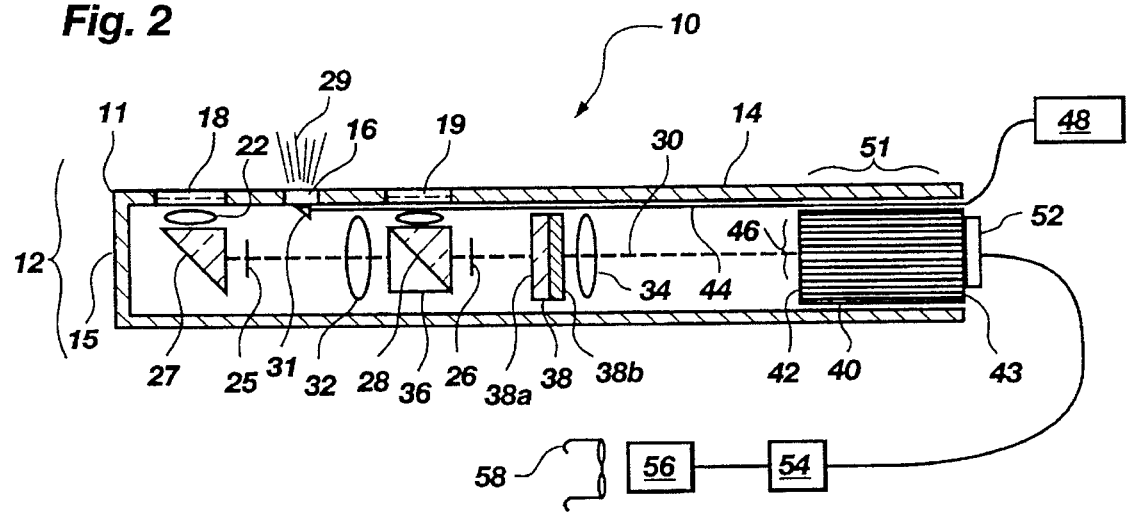
FIG. 2 is a side, cross sectional view of the stereo laparoscope of FIG. 1.

Referring to FIG. 2, there is shown a side, cross sectional view of the laparoscope 10, of FIG. 1. The laparoscope 10 further includes left and right objective lenses 22 and 23, and left and right mirrors 27 and 28, respectively. First and second image planes 25 and 26 lie along a common line of sight 30, as do stationary imaging lens 32, stationary focusing lens 34, polarizing beam splitter 36, optical switch 38, and the left and right mirrors 27 and 28. It can be seen in FIG. 2 that left and right mirrors 27 and 28 are diagonally positioned with respect to the common line of sight 30. A coherent, image-transmitting optical fiber bundle 40 having first and second opposite end faces 42 and 43, respectively, is also disposed within the casing 12. The first and second end faces 42 and 43 include image-receiving and image-transmitting fiber tips, respectively, the imagereceiving tips being shown at bracket 46. The bundle 40 is coherent in that the opposing tips of each fiber are located in substantially exactly the same positional orientation within the end faces 42 and 43, respectively, to prevent scrambling and distortion of the transmitting image. Light-emitting fibers 44 are disposed within the casing 12 and in contact with a prism 31, for providing light 29.

A preferred casing comprises a thin, elongate casing body 12 having a front-end face 15 and cylindrical walls 14. The portion of the casing 12 between the front-end face 15 and the first face 42 of the fiber bundle 40 must be rigid to maintain precise positioning of the imaging optics therein. The portion of the casing 12 containing the bundle 40 may be made from a soft, semi-rigid material so that it can be flexed and more easily inserted through irregular passages. The casing may alternatively comprise any cross sectional shape or material suitable for intracorporeal insertion and for housing the assembly to be contained therein.

The fiber bundle 40 comprises several hundred thousand image-transmitting fibers 46 each having a diameter of about 5 to 10 microns. The resolution of an image carried by the fiber bundle 40 is a function of the number of fibers present. At the present time, each fiber must be at least about five to ten microns in diameter in order to prevent light from escaping from the fiber. This minimum diameter requirement on the fibers, coupled with the number of fibers necessary to convey a high-quality optical image, necessitates a fiber bundle 40 having a diameter of approximately ten millimeters, and hence the casing 12 is approximately twelve millimeters in diameter. It is expected that these dimensions will decrease with time as the technology advances. However, any such dimensional limitations render the single-bundle arrangement discovered by the applicants advantageous relative to the two-bundle systems.

According to applicant's present knowledge, rigid fiber bundles offer image quality superior to that offered by flexible fiber bundles. The fibers 46 comprise a multi-compound glass fiber having an inner core for carrying light and outer cladding for keeping the light within the core. This is accomplished by using cladding which has a different index of refraction than the core material, thereby creating a light guide. The core has a higher index of refraction than the cladding. However, the fiber bundle 40 may alternatively comprise flexible fibers of multi-compound plastic, or any other optical fiber which would facilitate the purposes of the present invention.

The first and second end faces 42 and 43 comprise the tips of the coherent bundle of fibers 40. The fibers 46 are tightly fused together by their cladding at the first and second end faces 42 and 43 so that the same positional relationship of the fibers is maintained at said faces. The fibers preferably remain loose in the middle section, designated at bracket 51, but this is not required. The light-emitting fibers 44 may comprise a silicone resin, a multifiliment type plastic optical fiber or any other fibrous material suitable for transmitting light. The light-emitting fibers 44 may be spatially separated from the fiber bundle 40 as shown in FIG. 2, or may alternatively be mounted upon the bundle 40 or even incorporated within the bundle 40 itself, and will preferably comprise a bundle having a diameter of approximately one millimeter or less.

A fiberoptic light source 48 comprising an arc lamp is connected to the light-emitting fibers 44 for introducing light therein. The light source 48 may alternatively comprise a halogen lamp or any other light source suitable for introducing light into fiberoptic filaments. When the light source 48 is actuated, light is introduced into the fibers 44 which carry the light to the prism 31. The light 29 is reflected by prism 31 and thereby projected through the illuminating window 16, or may alternatively be so conveyed in any manner known to those skilled in the art. The light 29 then illuminates an object or region (not shown) external to the laparoscope 10 to thereby cause said external object to reflect light. The light reflected from the external object enables the left and right observation windows 18 and 19 to provide left-hand and right-hand points of view of said external object.

The left-hand point of view is processed by the left objective lens 22 into a left optical image. The left optical image is transmitted onto the first image plane 25 by the left mirror 27. Similarly, the right observation window 19 provides access to a right-hand point of view which is processed by the right objective lens 23 into a right optical image and transmitted onto the second image plane 26 by the right mirror 28. Both objective lenses 22 and 23 preferably have the same aperture and focal length.

The left and right mirrors 27 and 28 are positioned so that they project their respective images substantially along the common line of sight 30 such that they are superimposed upon second image plane 26. The left optical image from the first image plane 25 is collected by the stationary imaging lens 32 and projected onto the second image plane 26 with magnification so that the left and right optical images have substantially the same magnification when they are superimposed on second image plane 26. Both images pass through the polarizing beam splitter 36 in such a way that both images have opposing polarity. The optical switch 38 collects the left and right polarized optical images and alternately transmits them, i.e. one-at-a-time, onto the image-transmitting fibers 46 of the first end face 42 of the fiber bundle 40. The optical switch 38 includes a liquid crystal polarization rotator 38a and a linear polarizer 38b which operate as known in the art to accomplish the alternating transmission of the left and right polarized optical images. The image-transmitting fibers 46 carry the alternating left and right polarized optical images to the second end face 43.

The optical switch 38 preferably comprises a liquid crystal layer and is known in the art for the capacity to alternately block and transmit horizontally and vertically polarized images. The purpose of polarizing the two optical images is thus to allow the optical switch 38 to transmit the left and right images one at a time to the first end face 42 of the fiber bundle 40. The purpose of having a left image and a right image is to provide an optical image having depth, or the illusion of three dimensions.

Variable focusing can be achieved by causing the focusing lens 34 to be moveable along the line of sight 30 as will be described later in more detail. For fixed focus imaging, the focusing lens 34 can be fixed or eliminated.

A camera apparatus 54 is optically connected to the image-transmitting fibers 46 at the second end face 43, said connection represented by connecting structure 52. The camera receives the alternating left and right optical images from the second end face 43 in tandem with the optical switch 38 at said predetermined rate. The camera 54 presents the images as enlarged, alternating left-right video images on a monitor 56 shown schematically in FIG.2. The monitor displays the alternating images and the surgeon wears specialized glasses 58 having optical valves, such as Crystal-Eyes✢ glasses, to view the alternating images on the monitor 56.

The glasses 58 are simply two optical valves or shutters that transmit the images one at a time alternately to the left eye and the right eye in tandem with the optical switch 38 and monitor 56 at said predetermined rate. The predetermined rate of alternation is preferably controlled by a scan signal from the monitor 56, which controls the optical switch 38 in the stereo laparoscope and the optical valves in the glasses 58 with conventional video circuitry. This arrangement ensures that the optical switch, camera, monitor and optical valves operate in tandem and at the same rate. Thus, the left eye sees only images from the left observation window 18 of the endoscope and the right eye sees only images from the right observation window 19, creating a stereoscopic view. The rate of alternation is faster than the flicker-sensing limit of the human eye, resulting in flicker free viewing.

A unique aspect of the present invention is that the observation windows 18 and 19 are disposed in the side walls 14 of the casing 12 instead of in the front-end face 15. This window arrangement advantageously allows a user to position the side walls 14 adjacent to a desired intracorporeal viewing region for a transverse view, instead of requiring the front-end face 15 to face the viewing region. The transverse viewing arrangement also allows for a larger separation of distance between the windows 18 and 19 and associated lenses, while maintaining a smaller diameter of the housing 12. The window arrangement of the present invention thereby makes it easier for the user to view relatively remote intracorporeal regions, with a minimum of disturbance to surrounding tissue and organs.

Figure 4:
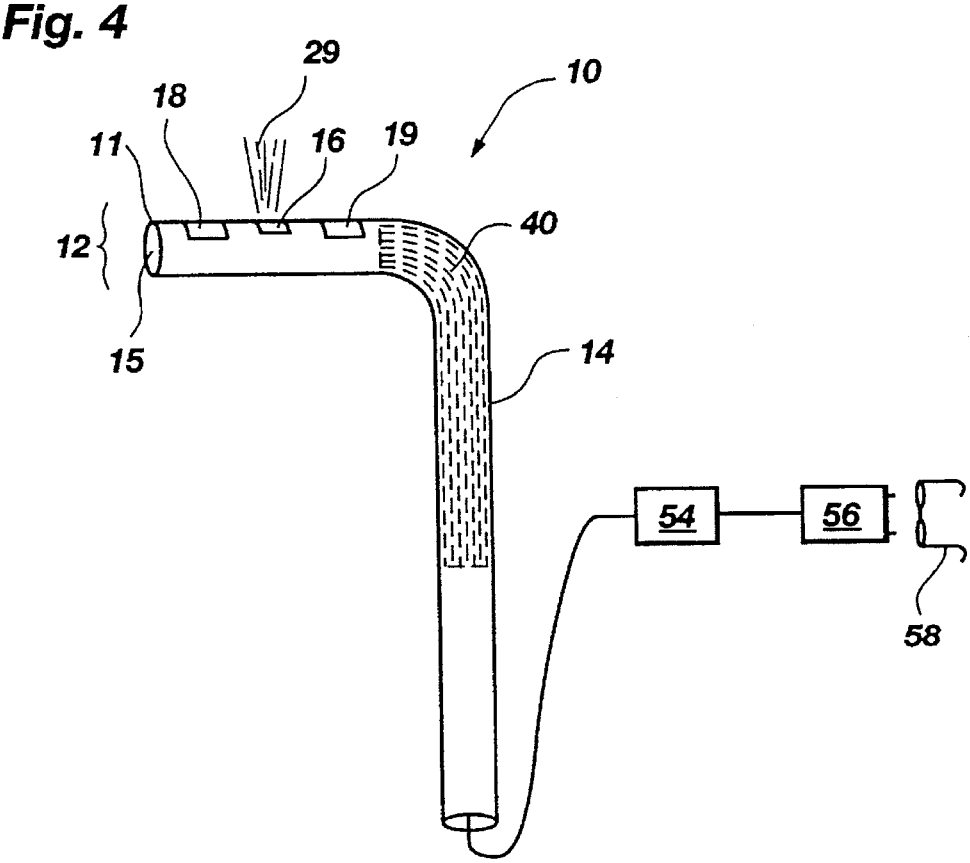
FIG. 4 is a perspective view of another alternative embodiment of the stereo laparoscope of FIG. 1 with an optical fiber bundle shown in phantom.

The embodiment presented in FIG. 2 illustrates the simplest embodiment, namely, a stereo laparoscope 10 comprising a rigid or semi-rigid straight casing 12 allowing observations at the right angle. However, the laparoscope may alternatively comprise a rigid or semi-rigid casing 14 bent at a 90 degree angle as shown in FIG. 4. As noted above, at least the portion of the casing 12 between the front-end face 15 and the fiber bundle 40 must be rigid in order to maintain precise positioning of the imaging optics therein. The embodiment of FIG. 4 allows for a straight forward observation while utilizing the fiberoptic advantage of transmitting an image around curves by using a curved fiber bundle, illustrated in phantom at 40 in FIG. 4. It is also within the scope of the present invention to use a flexible casing with a flexible fiber bundle to allow the physician to selectively flex the laparoscope in order to achieve a desired point of view.

The observation windows 18 and 19 are preferably arranged substantially in a row along the hollow casing 12, but may alternatively be arranged in some other configuration. Said observation windows may alternatively comprise three or more observation windows. The illuminating window 16 is lined up in the row with the observation windows 18 and 19, but may be arranged otherwise and may alternatively comprise two or more illuminating windows.

The most economical embodiment utilizes a single optical switch 38 positioned in the common line of sight 30 of two beams of light, as discussed above in conjunction with FIG. 2. However, the same effect could be accomplished with two separate light valves, one for each observation window 18 and 19, but at a higher cost. This alternative configuration offers improved contrast, and is discussed below in conjunction with FIG. 5.

Instead of using left and right objective lenses 22 and 23 to process the light into left and right optical images, optical imaging properties may be incorporated into the left In this and right observation windows 18 and 19. configuration, said windows 18 and 19 would serve the dual purpose of receiving the light reflected from an external object to be viewed, and processing the light received into left and right optical images. All lenses (i.e. objective lenses, imaging lenses, focusing lenses, and so forth) have been presented as single element components. However, the scope of the invention includes multi-element lenses as are known in the art for improving the image quality and otherwise optimizing the performance of the system.

The mirrors 27 and 28 and the beam splitter 36 have been presented in FIG. 2 in the form of prisms and a cube, respectively. The mirror 28 is actually a surface of the beam splitter 36. This is a preferred configuration. However, plane front surface mirrors and a flat beam splitter could be used without changing the basic concept of the invention.

The means for alternating the left and right optical images may also comprise apparatus other than the optical switch 38. For example, the observation windows 18 and 19 may comprise liquid crystal display (LCD), shutter-type windows designed to alternately block and receive light, or other windows which can be so designed. The shutter-type window element is shown schematically in FIG. 3 as phantom lines 18a and 19a. Such shutter-type windows essentially turn on and off as known in the art to alternately block and receive light. Electronic switching means would cause the windows to alternately block and receive light at a predetermined rate such that the left observation window 18 receives light while the right observation window 19 blocks light, and vice versa. The optical switch 38 would be unnecessary in this case. Other alternative embodiments include separate left and right polarizers, shown schematically in phantom line as items 36a and 36b in FIG. 1, for processing the light received from the left and right observation windows 18 and 19, respectively, into left and right polarized images of the intracorporeal region, with the images having opposing polarity, in lieu of the polarizing beam splitter 36.

Fixed focus optics are suitable for many applications of stereoscopic imaging, wherein the focusing lens 34 remains in a stationary position. However, adjustable focus is a useful feature for many of the demands of surgery and other medical procedures. Adjustable focus may be provided for the embodiment of FIG. 2 by designing the focusing lens 34 to be moveable along the line of sight 30 using mechanical or electrical remote control as is known in the art. The focus of the stereoscopic optical image produced by the laparoscope 10 would vary with variation of the movement of said focusing lens along the line of sight 30. Means for adjusting the focus may alternatively be implemented by translating the fiber bundle 40 along the line of sight 30 by manual or remote control.

Figure 3:
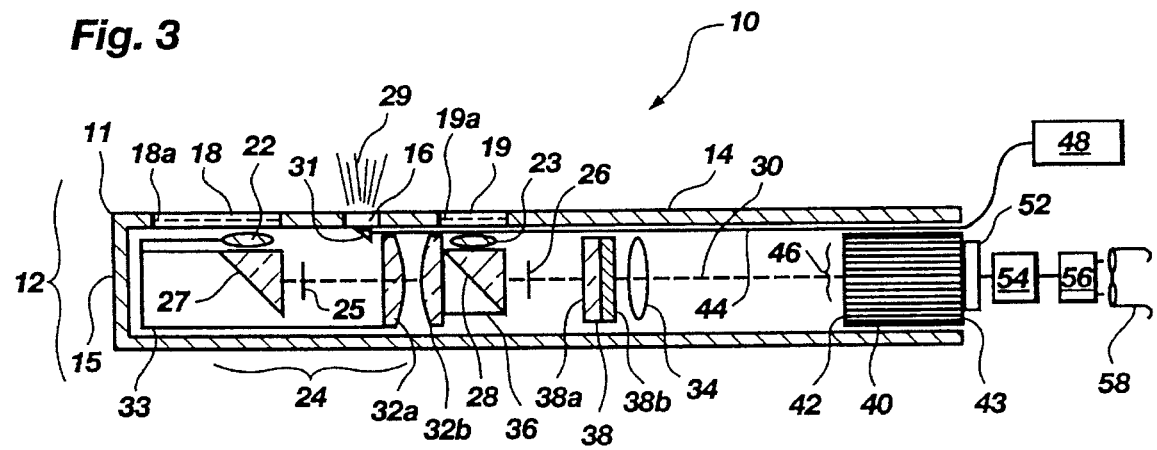
FIG. 3 is a side, cross sectional view of an alternative embodiment of the stereo laparoscope of FIG. 1.

The depth perception of the embodiment illustrated in FIG. 2 is non-variable since the left and right objective lenses 22 and 23 remain stationary and the distance therebetween is thus constant. In many applications this is sufficient. However, variable depth perception is desirable in some cases. This is achieved by a modification to the embodiment of FIG. 2, illustrated in FIG. 3. FIG. 3 shows a preferred embodiment of a stereo laparoscope which provides variable depth perception by essentially splitting the imaging lens 32 of FIG. 2 into two separate lenses. A moving assembly designated by bracket 24 comprises movable left objective lens 22, movable left mirror 27 and movable imaging lens 32a. The left observation window 18 is enlarged to accommodate the movement of the left objective lens 22. Imaging lens 32b is stationary. The left objective lens 22, the left mirror 27, and the imaging lens 32a move in tandem as a unit by means of mechanical or electrical remote control as is known in the art. A means for moving these elements in tandem is shown schematically in FIG. 3 as item 33. By translating the moving assembly 24 along the line of sight 30 as such, a stereoscopic optical image having variable depth perception is achieved.

Figure 5:
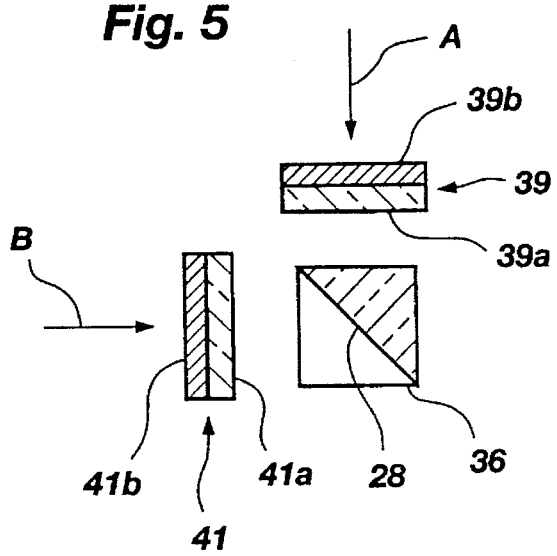
FIG. 5 is a schematic view of an alternative optical switching arrangement incorporating two optical valves.

An alternative design of the optical switching arrangement shown in FIGS. 2–3 is shown schematically in FIG. 5. Two optical switches 39 and 41 are positioned adjacent to the beam splitter 36 as shown. Arrow A represents the right image entering the optical switch 39, and arrow B represents the left image entering the optical switch 41. The left and right images are thereby alternated before entering the beam splitter 36, instead of after as in the embodiments of FIGS. 2–3. This alternative design offers better contrast and thus a higher quality stereoscopic view.

The method of use of the laparoscope 10 is quite simple. A physician makes a small incision in the abdominal cavity and inserts the distal end 11 of the laparoscope 10 therein so that said distal end resides within the abdominal cavity at a desired location. The physician can then inspect the location by viewing the three dimensional video image thereof displayed by the specialized glasses 58, rotating and otherwise maneuvering the laparoscope as desired in order to achieve an optimal view.

It is to be understood that scope of the invention includes replacing the fiber bundle 40 with any suitable image-carrying apparatus. For example, the bundle 40 could be replaced with a CCD camera chip as known in the art, allowing elimination of fiber bundles completely. This may prove advantageous, depending on the needs of the user. The smaller the CCD camera chip is, the more advantageous it becomes to substitute such a camera chip for the fiber bundle 40.

It is known in the art to rotate optical images electronically. The optical images produced in accordance with the present invention could be electronically rotated by 180 degrees, thereby allowing insertion of the laparoscope 10 from either side of a region to be viewed.

The present invention represents a significant advance over traditional apparatus and methods of stereoscopic viewing. It is noted that many of the advantages of the present invention accrue due to the placement of the observation windows in the side walls of the casing, and the combination of a relay lens system, an optical switch and a single light-transmitting and image-receiving fiber bundle within a conventional tubular casing. The problems associated with cost, weight, compactness and image quality are overcome to a significant degree by combination of an optical switch with a single fiberoptic bundle, and the placement of the observation windows in the side walls of the casing. Although the prior art apparatus and methods for stereoscopic viewing offer some of the advantages of fiberoptics and stereoscopic viewing, their disadvantages, including relatively high cost, weight and lack of compactness are overcome by the present invention's use of a single fiber bundle. Those skilled in the art will appreciate from the preceding disclosure that the objectives stated above are advantageously achieved by the present invention.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements.

What is claimed is:

1. A stereo laparoscope for producing a stereoscopic optical image of an intracorporeal region external to the laparoscope to human eyes, the laparoscope comprising:

a hollow elongate casing having side walls and an axial direction;

means coupled to the casing for illuminating the intracorporeal region to thereby cause said region to reflect light;

left and right observation windows disposed in the side walls of the casing for receiving light reflected from the intracorporeal region to thereby provide left and right points of view of said region; and means for processing the light received into a stereoscopic optical image of the intracorporeal region;

light emitting means disposed within the hollow casing for emitting light; and an illuminating window disposed in the side walls of the casing for projecting said emitted light onto the intracorporeal region to thereby cause said region to reflect light;

wherein the means for processing further comprises:

imaging means coupled to the casing for processing the light received into left and right optical images of the intracorporeal region, respectively, said optical images having left and right points of view;

left and right mirrors disposed within the casing for reflecting said left and right optical images within the casing in the axial direction and along a common line of sight such that said images become superimposed upon each other at some point;

an imaging lens disposed within the casing between the left and right mirrors for collecting and magnifying one of said optical images to thereby cause said left and right optical images to have substantially the same magnification when they become superimposed upon each other;

a polarizing beam splitter disposed within the casing along said common line of sight for receiving the left and right optical images, and for polarizing said images such that said left and right optical images have opposing polarity, respectively, and transmitting said left and right polarized optical images further along the common line of sight;

at least one optical switch disposed within the casing for receiving said polarized optical images and alternately blocking said left polarized optical image while transmitting said right polarized optical image and blocking said right polarized optical image while transmitting said left polarized optical image, at a predetermined rate; and a single optical fiber bundle disposed within the casing and having a first end face, a second end face and fibers for receiving said alternating left and right polarized optical images at said first end face and carrying them one at a time to said second end face to thereby produce a stereoscopic optical image of the intracorporeal region.

2. A stereo laparoscope as in claim 1 wherein the means for illuminating further comprise:

light emitting means disposed within the hollow casing for emitting light; and an illuminating window disposed in the side walls of the casing for projecting said emitted light onto the intracorporeal region to thereby cause said region to reflect light.

3. A stereo laparoscope as in claim 2 wherein the observation windows are positioned substantially in a row along the casing in the axial direction.

4. A stereo laparoscope as in claim 3 wherein the illuminating window is positioned substantially in the same row with the observation windows.

5. A stereo laparoscope as in claim 1 wherein the means for illuminating further comprise:

light emitting means disposed within the hollow casing for emitting light; and a plurality of illuminating windows disposed in the side walls of the casing for projecting said emitted light onto the intracorporeal region to thereby cause said region to reflect light.

6. A stereo laparoscope as in claim 1 wherein the predetermined rate of alternation is faster than the flicker-sensing limit of human eyes, to thereby provide flicker free viewing.

7. A stereo laparoscope as in claim 1 wherein the imaging means are incorporated into said left and right observation windows such that said observation windows receive light reflected from the intracorporeal region and process the light received into left and right optical images, respectively, of said region.

8. A stereo laparoscope as in claim 1 wherein the imaging means further comprise left and right objective lenses disposed within the casing for processing the light received from the left and right observation windows, respectively, into left and right optical images of the intracorporeal region.

9. A stereo laparoscope as in claim 1 further comprising a handle grip disposed on the side walls of the casing and extending radially outward therefrom.

10. A stereo laparoscope for producing a stereoscopic optical image of an intracorporeal region external to the laparoscope comprising:

a hollow, elongate casing having an axial direction;

means for illuminating the intracorporeal region to thereby cause said region to reflect light;

a plurality of observation windows disposed in the casing for receiving light reflected from the intracorporeal region to thereby provide left and right points of view of said region;

a single optical fiber bundle disposed within the casing and having a first end, a second end and fibers for receiving optical images at said first end;

light imaging means disposed within the casing for processing the light received from each observation window into left and right optical images of the intracorporeal region and causing said optical images to be received by the receiving fibers at the first end of the fiber bundle and carried to the second end to thereby produce a stereoscopic optical image of said region; and variable depth perception means disposed in the casing for varying the depth perception of the stereoscopic optical image.

11. A stereo laparoscope as in claim 10 the means for illuminating further comprising:

means for emitting light within the casing; and at least one illuminating window disposed in the casing for conveying the emitted light onto the intracorporeal region to thereby cause said region to reflect light.

12. A stereo laparoscope as in claim 10 wherein the casing further comprises side walls and wherein said plurality of observation windows are disposed in said side walls and positioned substantially in a row along the casing in the axial direction.

13. A stereo laparoscope as in claim 10 wherein the light imaging means further comprise focusing means for adjusting the focus of the stereoscopic optical image.

14. A stereo laparoscope as in claim 13 wherein the focusing means further comprise a moveable focusing lens disposed within the casing for collecting the left and right optical images and projecting them onto the first end of the fiber bundle to thereby cause said images to be received by the receiving fibers and carried to the second end of the fiber bundel, the focus of the stereoscopic optical image varying with variation of the movement of said focusing lens.

15. A stereo laparoscope as in claim 13 wherein the first end of the fiber bundle is moveable in the axial direction such that the focusing means are incorporated into the fiber bundle, the focus of the stereoscopic optical image varying with variation of movement of said first end of the fiber bundle in the axial direction.

16. A stereo laparoscope for producing a stereoscopic optical image of an intracorporeal region external to the laparoscope, said laparoscope comprising:

a hollow elongate casing having an axial direction;

means for illuminating the intracorporeal region to thereby cause said region to reflect light;

left and right observation windows disposed in the casing for receiving light reflected from the intracorporeal region to thereby provide left and right points of view of said region;

an optical fiber bundle disposed within the casing and having a first end, a second end and fibers for receiving optical images at said first end;

light imaging means disposed within the casing for processing the light received from each observation window into left and right optical images of the intracorporeal region and causing said optical images to be received by the receiving fibers at the first end of the fiber bundle and carried to the second end to thereby produce a stereoscopic optical image of said region;

left and right objective lenses disposed within the casing for processing the light received by the left and right observation windows, respectively, into left and right optical images of the intracorporeal region, the left objective lens being movable in the axial direction;

left and right reflective means disposed within the casing and diagonally relative to the axial direction for reflecting said left and right optical images within the casing in the axial direction and along a common line of sight such that said images become superimposed upon each other at some point, the left reflective means being movable in the axial direction;

a stationary magnifying means disposed within the casing between the left and right reflective means and in the common line of sight for collecting and magnifying the left optical image to thereby cause said left and right optical images to have substantially the same magnification when they become superimposed upon each other; a movable image transmitting means disposed within the casing between the left reflective means and the stationary magnifying means and in the common line of sight such that the left image passes through said movable image transmitting means before passing through the stationary magnifying means;

variable depth perception means comprising:
the movable left objective lens;
the moveable left reflective means;
the movable image transmitting means; and
means for moving said movable left objective lens, left reflective means and moveable image transmitting means in the axial direction to thereby enable a three-dimensional optical image of the intracorporeal region having variable depth perceptibility, a perception of depth of said three-dimensional optical image varying with variation of the movement of the left objective lens, left reflective means and moveable image transmitting means.

17. A stereo laparoscope as in claim 10, wherein the plurality of observation windows comprise left and right shutter windows, each said shutter window capable of alternately blocking and receiving light reflected from the intracorporeal region, the light imaging means further comprising:

left and right lenses disposed within the casing for processing the light received from the left and right observation windows, respectively, into left and right optical images of the intracorporeal region; and window switching means for alternately causing the left shutter window to block light while the right shutter window receives light and the right shutter window to block light while the left shutter window receives light, at a predetermined rate, such that the receiving fibers alternately receive said left and right optical images at said predetermined rate, and carry said alternating optical images one at a time to the second end of the fiber bundle.

18. A stereo laparoscope as in claim 16, wherein the left and right reflective means comprise left and right mirrors, respectively, and wherein the stationary magnifying means comprises a stationary imaging lens, and wherein the movable image transmitting means comprises a movable imaging lens, and wherein the casing further comprises side walls and wherein said left and right observation windows are disposed in said side walls and positioned substantially in a row along the casing in the axial direction.

19. A stereo laparoscope as in claim 16, wherein the means for moving comprises means for moving the movable left objective lens, left reflective means and moveable image transmitting means in tandem in the axial direction.

20. A stereo laparoscope as in claim 10, wherein the plurality of observation windows comprise left and right observation windows, the light imaging means further comprising:

polarizing means disposed within the casing for polarizing the left and right optical images of the intracorporeal region such that said left and right images have opposing polarity; and optical switching means disposed within the casing for receiving said left and right polarized optical images and alternately blocking said left polarized optical image while transmitting said right polarized optical image and blocking said right polarized optical image while transmitting said left polarized optical image, at a predetermined rate, such that said alternating optical images are received one at a time by the receiving fibers at the first end of the fiber bundle and carried one at time through said receiving fibers to the second end at each predetermined rate.

21. A stereo laparoscope as in claim 20, wherein the polarizing means further comprise a polarizing beam splitter.

22. A stereo laparoscope as in claim 20, wherein the polarizing means further comprise:

left and right polarizing beam splitters disposed within the casing for processing the light received from the left and right observation windows, respectively, into left and right polarized images of the intracorporeal region, said images having opposing polarity.

23. A stereo scope for producing a stereoscopic optical image of a region external to the scope to human eyes having a flicker-sensing limit, the stereo scope comprising:

a hollow casing having side walls;

a single optical fiber bundle disposed within the casing and having a first end, a second end and fibers for receiving optical images at said first end;

means for illuminating the external region comprising:
light-emitting fibers disposed within the casing for emitting light within the casing;
at least one illuminating window disposed in the casing for conveying the emitted light onto the external region to thereby cause said region to reflect light; and means for reflecting the emitted light from the casing through said illuminating window;

left and right observation windows disposed in the side walls of the casing thereof for receiving light reflected from the external region to thereby provide left and right points of view of said region; and light imaging means coupled to the casing for processing the light received from each observation window into left and right optical images of the external region and causing said optical images to be received by the receiving fibers at the first end of the fiber bundle and carried to the second end to thereby produce a stereoscopic optical image of said external region, the light imaging means including:

polarizing means disposed within the casing for polarizing the left and right optical images of the external region such that said left and right images having opposing polarity;

an optical switch disposed within the casing for receiving said left and right polarized optical images and alternately blocking said left polarized optical image while transmitting said right polarized optical image and blocking said right polarized optical image while transmitting said left polarized optical image, at a predetermined rate, such that said alternating optical images are received one at a time by the receiving fibers at the first end of the fiber bundle and carried one at a time through said receiving fibers to the second end at said predetermined rate, wherein the predetermined rate of alternation is faster than the flicker-sensing limit of human eyes to thereby provide flicker free viewing;

focusing means coupled to the casing for adjusting the focus of the stereoscopic optical image; and variable depth perception means for varying the depth perception of the stereoscopic optical image.

24. A stereo laparoscope for producing a stereoscopic optical image of an intracorporeal region external to the laparoscope comprising:

a hollow elongate casing having an axial direction;

means for illuminating the intracorporeal region to thereby cause said region to reflect light;

a plurality of observation windows disposed in the casing for receiving light reflected from the intracorporeal region to thereby provide left and right points of view of said region;

a single image guide disposed within the casing for receiving and transmitting optical images; and light imaging means disposed within the casing for processing the light received from the observation windows into left and right optical images of the intracorporeal region and causing said optical images to be received by the image guide to permit said image guide to transmit said left and right optical images to thereby produce a stereoscopic optical image of said region, said light imaging means including:

a first light receiving means for receiving first light from one of the windows and transmitting said first light;

a second light receiving means for (i) simultaneously receiving the first light from the first light receiving means and a second light from another of the windows and (ii) simultaneously transmitting both the first and second light toward the image guide.

25. A stereo laparoscope as in claim 24, wherein said second light receiving means transmits said optical images in a superimposed orientation toward the image guide.

26. A stereo laparoscope for producing a stereoscopic optical image of an intracorporeal region external to the laparoscope comprising:

a hollow elongate casing having an axial direction;

means for illuminating the intracorporeal region to thereby cause said region to reflect light;

a plurality of observation windows disposed in the casing for receiving light reflected from the intracorporeal region to thereby provide left and right points of view of said region;

an image guide disposed within the casing and having an image-receiving end for receiving and transmitting optical images; and light imaging means disposed within the casing for processing the light received from the observation windows into left and right optical images of the intracorporeal region and causing said optical images to be received by the image guide to permit said image guide to transmit said left and right optical images to thereby produce a stereoscopic optical image of said region, said light imaging means including first and second reflective light-receiving means for receiving and reflecting light received from the windows along a common light path, wherein said first and second reflective light-receiving means and the image-receiving end of the image guide are all positioned within the casing along a common, linear line of alignment.

27. A stereo laparoscope as in claim 26, wherein the image guide comprises a single, optical fiber bundle.

28. A stereo laparoscope as in claim 26, wherein the image guide comprises a single camera chip.

29. A stereo laparoscope for producing a stereoscopic optical image of an intracorporeal region external to the laparoscope comprising:

a hollow elongate casing having an axial direction;

means for illuminating the intracorporeal region to thereby cause said region to reflect light;

a plurality of observation windows disposed in the casing for receiving light reflected from the intracorporeal region to thereby provide left and right points of view of said region;

a single image guide disposed within the casing for receiving and transmitting optical images; and light imaging means disposed within the casing for processing the light received from the observation windows into left and right optical images of the intracorporeal region and causing said optical images to be received by the image guide to permit said image guide to transmit said left and right optical images to thereby produce a stereoscopic optical image of said region, said light imaging means including means for transmitting said left and right optical images in a superimposed orientation along a single optical path toward the image guide.

* * * * *